United States Patent
Eom et al.

(10) Patent No.: US 9,895,078 B2
(45) Date of Patent: Feb. 20, 2018

(54) BODY IMPEDANCE MEASURING APPARATUS AND BODY COMPOSITION ANALYSIS SYSTEM INCLUDING THE SAME

(71) Applicant: SAMSUNG ELECTRONICS CO., LTD., Suwon-si (KR)

(72) Inventors: Kunsun Eom, Seoul (KR); Jungmok Bae, Seoul (KR); Kak Namkoong, Seoul (KR); Yeolho Lee, Anyang-si (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 70 days.

(21) Appl. No.: 14/677,014

(22) Filed: Apr. 2, 2015

(65) Prior Publication Data

US 2016/0081581 A1 Mar. 24, 2016

(30) Foreign Application Priority Data

Sep. 24, 2014 (KR) .................. 10-2014-0127684

(51) Int. Cl.
*A61B 5/053* (2006.01)
*A61B 5/00* (2006.01)
*A61B 5/22* (2006.01)

(52) U.S. Cl.
CPC .......... *A61B 5/0537* (2013.01); *A61B 5/0004* (2013.01); *A61B 5/224* (2013.01); *A61B 5/4872* (2013.01); *A61B 5/4878* (2013.01)

(58) Field of Classification Search
None
See application file for complete search history.

(56) References Cited

U.S. PATENT DOCUMENTS 6,694,182 B1 * 2/2004 Yamazaki .......... A61B 5/02438
600/547
8,180,425 B2 * 5/2012 Selvitelli ............ A61B 5/04085
600/382

(Continued)

FOREIGN PATENT DOCUMENTS

JP 3522543 B2 4/2004
JP 3975000 B2 9/2007

(Continued)

OTHER PUBLICATIONS

Machine English Translation of JP 3975000.*

*Primary Examiner* — Jermele M Hollington
*Assistant Examiner* — Douglas X Rodriguez
(74) *Attorney, Agent, or Firm* — Sughrue Mion, PLLC

(57) ABSTRACT

A body impedance measuring apparatus includes: a first module including a first input electrode and a first output electrode which are configured to contact a subject; a second module including a second input electrode and a second output electrode which are configured to contact the subject; a connection member configured to connect the first module to the second module and adjust a distance between the first module and the second module; and a measuring unit configured to apply a current to the first and second input electrodes, detect a voltage between the first and second output electrodes, and determine a body impedance of a subject based on the detected voltage. At least a component of the measuring unit is disposed in the first module and is electrically connected to the second module through the connection member.

13 Claims, 8 Drawing Sheets

(56) References Cited

U.S. PATENT DOCUMENTS

| | | | | |
|---|---|---|---|---|
| 8,700,118 | B2* | 4/2014 | Oster | A61B 5/0002 600/372 |
| 8,836,345 | B2* | 9/2014 | Chetham | A61B 5/053 324/649 |
| 2003/0187363 | A1* | 10/2003 | Alroy | A61B 5/0006 600/509 |
| 2009/0264790 | A1* | 10/2009 | Ashida | A61B 5/0537 600/547 |
| 2010/0121216 | A1* | 5/2010 | Hamaguchi | A61B 5/0537 600/547 |
| 2015/0272503 | A1* | 10/2015 | Molden | A61B 5/6838 600/386 |

FOREIGN PATENT DOCUMENTS

| | | |
|---|---|---|
| KR | 10-2002-0026338 A | 4/2002 |
| KR | 10-2004-0008746 A | 1/2004 |
| KR | 10-1179997 B1 | 9/2012 |

\* cited by examiner

BODY IMPEDANCE MEASURING APPARATUS AND BODY COMPOSITION ANALYSIS SYSTEM INCLUDING THE SAME

CROSS-REFERENCE TO RELATED APPLICATION

This application claims priority from Korean Patent Application No. 10-2014-0127684, filed on Sep. 24, 2014 in the Korean Intellectual Property Office, the disclosure of which is incorporated herein in its entirety by reference.

BACKGROUND

1. Field

Apparatuses and methods consistent with exemplary embodiments relate to a body impedance measuring apparatus and a body composition analysis system including the same.

2. Description of the Related Art

With the development of medical technologies and the increase in the average lifespan, there is a growing interest in health care. In this regard, there is also a growing interest in medical devices, and applications of medical devices have increased. Examples of such medical devices include medical devices used in hospitals or medical examination centers, small and medium medical devices installed in public institutions, and small medical devices and health care devices that are owned or carried by individuals.

A body composition measuring device is a type of health care device that measures body composition by using bio-electrical impedance analysis (BIA). BIA is a method of calculating body fat content and body water content by using a difference in electrical resistance between non-fat tissue and fat tissue when a high alternating current (AC) wave having low energy passes through a body. BIA allows an electric current to flow through the body by taking into account that the body is a combination of impedances, measures a voltage through the current, and measures the impedance of the body based on the current and the voltage. The body composition measuring device needs to be made compact. Research has been conducted to miniaturize body composition measuring devices.

SUMMARY

Exemplary embodiments provide body impedance measuring apparatuses configured to measure body impedances of various portions of a subject and body composition analysis systems including the same.

According to an aspect of an exemplary embodiment, there is provided a body impedance measuring apparatus including: a first module including a first input electrode and a first output electrode which are configured to contact a subject; a second module including a second input electrode and a second output electrode which are configured to contact the subject; a connection member configured to connect the first module to the second module and adjust a distance between the first module and the second module; and a measuring unit configured to apply a current to the first and second input electrodes, detect a voltage between the first and second output electrodes, and determine a body impedance of the subject based on the detected voltage At least one component of the measuring unit is disposed in the first module and is electrically connected to the second module through the connection member.

The connection member may include at least one wire which is extendable and retractable to adjust the distance between the first module and the second module.

The measuring unit is further configured to measure the distance between the first module and the second module, the apparatus further comprising a display configured to display the determined body impedance and a body size of the subject that corresponds to the measured distance.

The connection member may include a first wire configured to connect the measuring unit to the second input electrode, and a second wire configured to connect the measuring unit to the second output electrode.

The connection member may include: a rotatable member around which a cable is wound, and a restoring member configured to exert a restoring force according to a rotation of the rotatable member.

The restoring member may exert a restoring force when the distance between the first module and the second module is increased by an external force, and the distance between the first module and the second module may be reduced by the restoring force when the external force is removed.

The first module may come into contact with the second module when the external force is removed.

The measuring unit may include: a current supply configured to supply a current to the first and second input electrodes; a voltage detector configured to detect the voltage between the first and second output electrodes; and an impedance calculator configured to calculate the body impedance of the subject from the voltage, wherein at least one of the current supply, the voltage detector and the impedance calculator is disposed in the first module.

The body impedance measuring apparatus may be portable.

At least one of the first module and the second module may be configured to contact at least one of a hand or a foot of the subject.

The first module may be foldable in a state in which the first input electrode and the first output electrode are exposed outside the apparatus.

The body impedance measuring apparatus may further include a patch configured to fix the first and second modules while maintaining the distance between the first module and the second module constant, wherein the patch is detachable from the subject.

The body impedance measuring apparatus may further include a transmitter configured to transmit information of the body impedance to an external device.

According to another aspect of an exemplary embodiment, a body composition analysis system includes: a measuring apparatus including a first module and a second module, each of the first module and the second module including an input electrode and an output electrode which are configured to contact a subject, a connection member configured to connect the first module to the second module and adjust a distance between the first module and the second module, and a measuring unit configured to supply a current to the input electrodes, detect a voltage between the output electrodes, and determine a body impedance of the subject; and an analysis apparatus configured to provide a protocol of using the measuring apparatus for determining the body impedance.

The analysis apparatus may receive information of the body impedance from the measuring apparatus through wireless communication and analyze body composition of the subject based on the information of the body impedance.

The body composition may include at least one of a body fat mass, a skeletal muscle mass, a muscle mass, a fat index, a muscle strength, edema, a body composition ratio, and a visceral fat mass.

The analysis apparatus may include a display configured to display the body composition.

The analysis apparatus may include a user interface configured to receive an input of at least one selected from a weight, an age, a gender and a height of the subject.

The analysis apparatus may be a mobile terminal.

At least a portion of the measuring unit may be disposed in the first module and be electrically connected to the second module through the connection member.

The connection member may include a first wire configured to connect the measuring unit to the second input electrode, and a second wire configured to connect the measuring unit to the second output electrode.

The connection member may include: a rotatable member around which a cable is wound, and a restoring member configured to exert a restoring force according to a rotation of the rotatable member.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
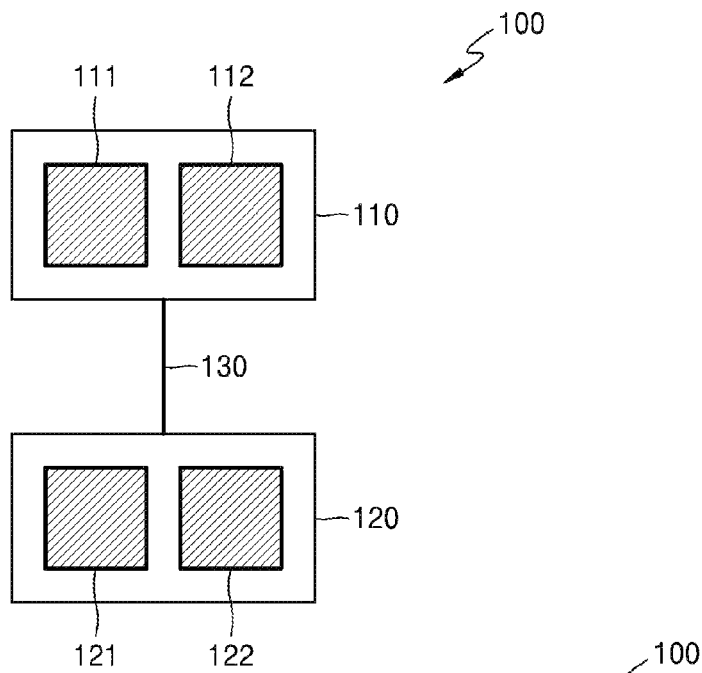
FIG. 1 is a schematic diagram of a body impedance measuring apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Figure 2:
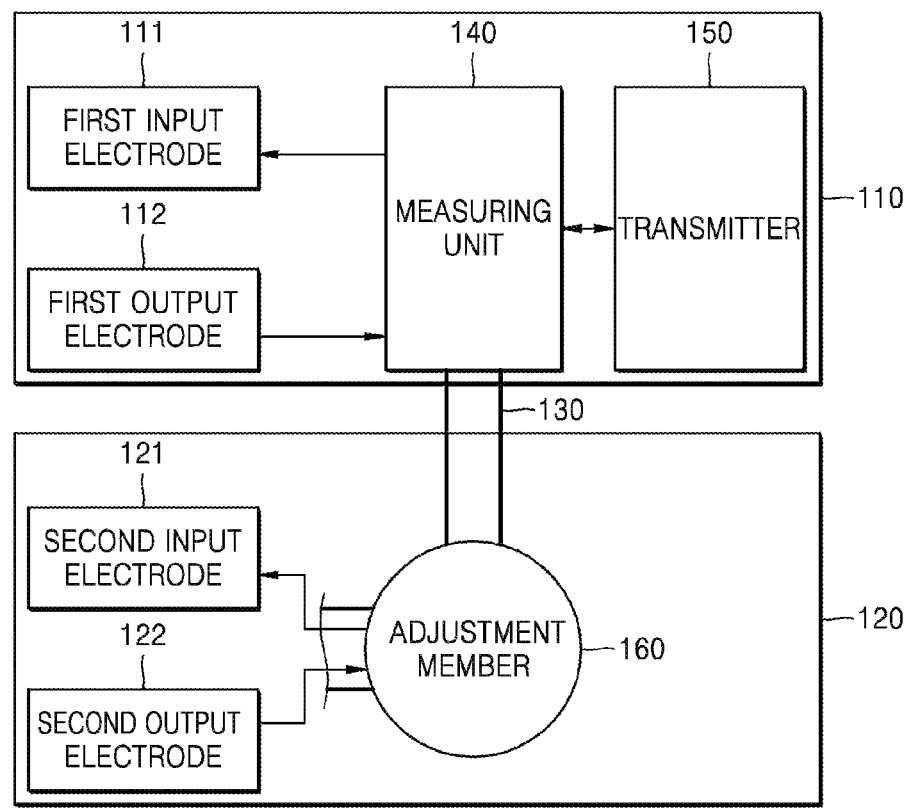
FIG. 2 is a block diagram of the body impedance measuring apparatus of FIG. 1.
Figure 3:
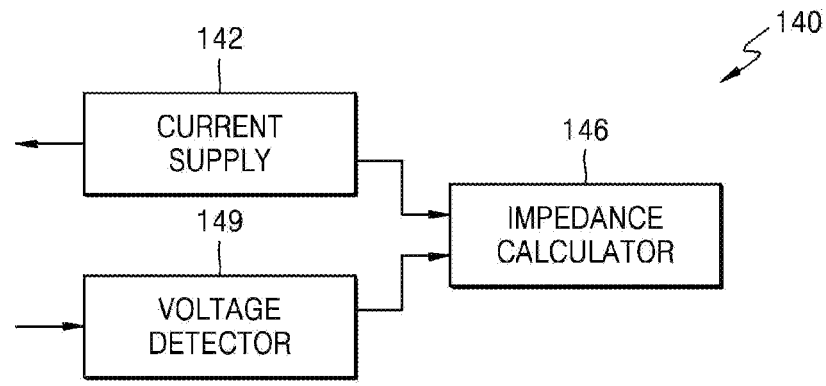
FIG. 3 is a block diagram of a measuring unit of the body impedance measuring apparatus of FIG. 2.
Figure 4:
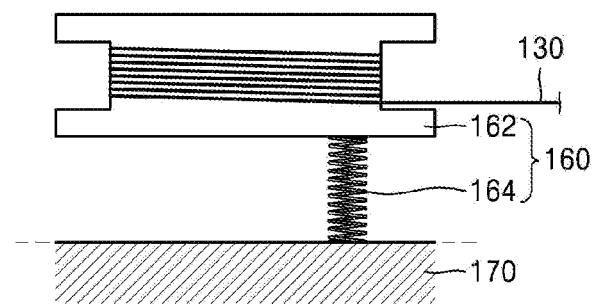
FIG. 4 is a diagram of a body impedance adjustment member of FIG. 2.

FIG. 1 is a schematic diagram of a body impedance measuring apparatus 100 according to an exemplary embodiment, FIG. 2 is a block diagram of the body impedance measuring apparatus 100 of FIG. 1, FIG. 3 is a block diagram of a measuring unit 140 of the body impedance measuring apparatus 100 of FIG. 2, and FIG. 4 is a diagram of an adjustment member 160 of FIG. 2. As illustrated in FIGS. 1 and 2, the body impedance measuring apparatus 100 may include a first module 110 and a second module 120. The first module 110 may include a first input electrode 111 and a first output electrode 112, and the second module 120 may include a second input electrode 121 and a second output electrode 122. The first and second modules 110 and 120 may be large enough to be grabbed by a subject with the subject's hand or to make contact with the subject's foot.

The first input electrode 111 and the first output electrode 112 may be exposed to the outside of the first module 110 and configured to contact the subject. The second input electrode 121 and the second output electrode 122 may be exposed to the outside of the second module 120 and configured to contact the subject. The first and second input electrodes 111 and 121 and the first and second output electrodes 112 and 122 may be a pad-type electrode so as to facilitate contact with the subject, but are not limited thereto. In FIG. 1, one first input electrode 111, one first output electrode 112, one second input electrode 121, and one second output electrode 122 are illustrated. However, an exemplary embodiment is not limited thereto and the first and second input and output electrodes 111, 112, 121, and 122 may be plural.

In this case, the subject is a target of which the body impedance is to be measured. The subject may include a person, an animal, or a part of the person or the animal. A user may be a subject, that is, a target of which the body impedance is to be measured, or a person that is able to use the body impedance measuring apparatus 100, such as a medical expert or the like. A user is a broader concept than a subject.

The body impedance measuring apparatus 100 may further include a connection member 130 that connects the first and second modules 110 and 120. The connection member 130 connects the first and second modules 110 and 120 mechanically and/or electrically. The connection member 130 may include a cable including one or more wires.

The body impedance measuring apparatus 100 may further include the measuring unit 140 that applies a current to the first and second input electrodes 111 and 121, receives a voltage between the first and second output electrodes 112 and 122, and measures a body impedance based on the current and the voltage. As illustrated in FIG. 3, the measuring unit 140 may include a current supply 142 that supplies the current to the first and second input electrodes 111 and 121, a voltage detector 149 that detects the voltage between the first and second output electrodes 112 and 122, and an impedance calculator 146 that calculates the body impedance of the subject by using the input current and the detected voltage. The voltage detector 149 may include an operational amplifier that amplifies the voltage between the first and second output electrodes 112 and 122, a filter that removes noise, and the like.

According to another embodiment, the measuring unit 140 may be included in the first and second module 110 and 120. For example, the current supply 142, the voltage detector 149, and the impedance calculator 146 of the measuring unit 140 may be disposed in the first module 110 and be electrically connected to the second module 120 through the connection member 130. However, an exemplary embodiment is not limited thereto. For example, the current supply 142 of the measuring unit 140 may be disposed in the first module 110, and the voltage detector 149 and the impedance calculator 146 may be disposed in the second module 120. The current supply 142 may be electrically connected to the second module 120 through the connection member 130, and the voltage detector 149 and the impedance calculator 146 may be electrically connected to the first module 110 through the connection member 130.

The body impedance measuring apparatus 100 may further include a transmitter 150 that provides the measured body impedance to an external apparatus. The transmitter 150 may be connected to the external apparatus by wire or wirelessly. For example, the transmitter 150 may perform Bluetooth communication with the external apparatus. The external apparatus may be an analysis apparatus 200 that analyzes the body composition of the subject by using the body impedance. Although not illustrated, the body impedance measuring apparatus 100 may further include a power supply that supplies power to the components of the body impedance measuring apparatus 100, and the power supply may be included in one of the first and second modules 110 and 120.

The connection member 130 may connect the first and second modules 110 and 120 mechanically and/or electrically. The connection member 130 may include a cable including one or more wires. For example, when the measuring unit 140 is disposed in the first module 110, the connection member 130 may include a first wire that connects the measuring unit 140 to the second input electrode 121, and a second wire that connects the measuring unit 140 to the second output electrode 122.

On the other hand, a distance between the first module 110 and the second module 120 may be adjustable by the adjustment member 160. As illustrated in FIG. 4, the connection member 130 may be wound around the adjustment member 160. The adjustment member 160 may include a rotatable member 162 and a restoring member 164 that provides a restoring force according to a rotation of the rotatable member 162. The rotatable member may include a pulley, and the restoring member 164 may include a spring.

As illustrated in FIG. 4, one end of the restoring member 164 may be fixed to a fixing member 170 disposed in the first module 110, and the other end of the restoring member 164 may be connected to the rotatable member 162. The connection member 130 may be wound around a side portion of the rotatable member 162. When an external force is applied to the first and second modules 110 and 120, the rotatable member 162 is rotated and the restoring member 164 exerts the restoring force according to the rotation of the rotatable member 162. For example, in a state in which the user grips the first and second modules 110 and 120, the user may apply a force so as to increase the distance between the first module 110 and the second module 120. Therefore, the rotatable member 162 is rotated in a first direction, and accordingly, the connection member 130 may be pulled out from the rotatable member 162 to increase the distance between the first module 110 and the second module 120.

The connection member 130 may be retractable. For example, when the external force applied to the first and second modules 110 and 120 is reduced or removed, the rotatable member 162 rewinds the connection member 130 while rotating in a direction opposite to the first direction. In other words, the connection member 130 may be rolled up around the rotatable member 162 with the aid of a spring return mechanism of the restoring member 152 to decrease the distance between the first module 110 and the second module 120.

Figure 5A:
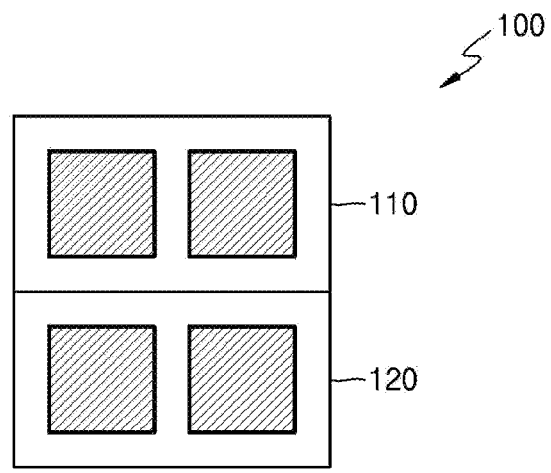
FIGS. 5A and 5B are diagrams of a distance between a first module and a second module.
Figure 5B:
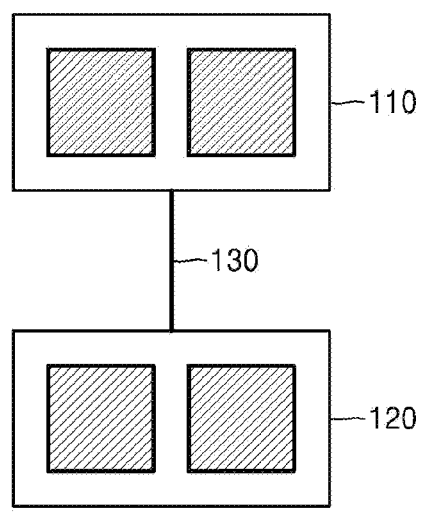

FIGS. 5A and 5B are diagrams illustrating a distance between the first module 110 and the second module 120. When no external force is applied to the first and second modules 110 and 120, the first and second modules 110 and 120 may stay in contact with each other, as illustrated in FIG. 5A. Since the first and second modules 110 and 120 stay in contact with each other when no external force is applied to the first and second modules 110 and 120, the volume of the body impedance measuring apparatus 100 is small. Therefore, it is convenient to keep and carry the body impedance measuring apparatus 100.

In addition, when an external force is applied to the first and second modules 110 and 120, the distance between the first module 110 and the second modules 120 is increased according to the magnitude of the external force. FIG. 5B is a diagram illustrating a state in which the first module 110 is spaced apart from the second module 120. The maximum distance between the first module 110 and the second module 120 depends on the length of the connection member 130, and the distance between the first module 110 and the second module 120 may be adjusted by the adjustment member 160. Since the distance between the first module 110 and the second module 120 is freely adjusted, the body impedance measuring apparatus 100 according to the exemplary embodiment may measure impedances at various portions of the subject. In addition, the body information of the subject, such as the height, leg length, and waist size of the subject, may be measured by using the distance between the first module 110 and the second module 120. Specifically, the measuring unit 140 may measure the distance between the first module 110 and the second module 120 to provide information of a body size corresponding to the measured distance. For example, when the connection member 130 wraps around the waist of the subject, the distance between the first module 110 and the second module 120 may correspond to the waist circumference of the subject. The information of the body size may be displayed along with the body impedance of the subject.

FIGS. 6A to 6E are diagrams of a method of measuring a body impedance by the body impedance measuring apparatus 100, according to an exemplary embodiment.

Figure 6A:
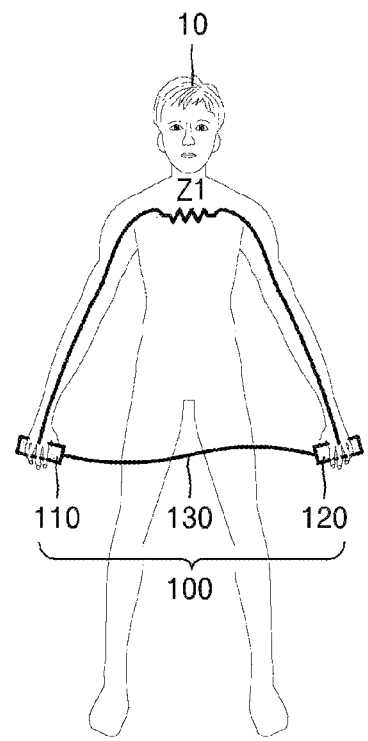
FIGS. 6A to 6E are diagrams of a method of measuring a body impedance by using a body impedance measuring apparatus, according to an exemplary embodiment.
Figure 6B:
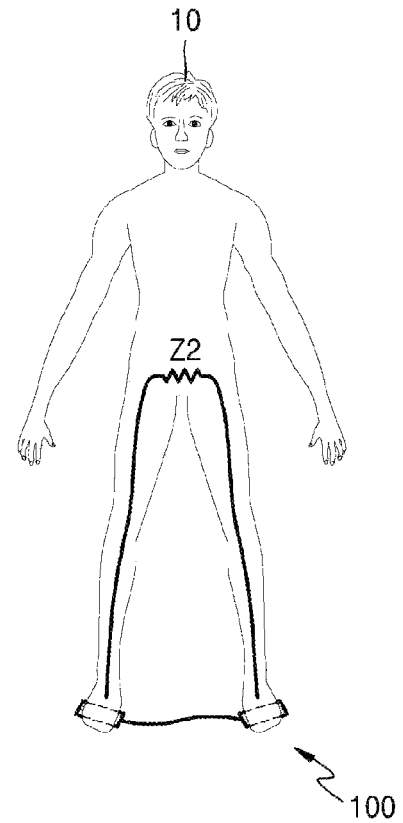
Figure 6C:
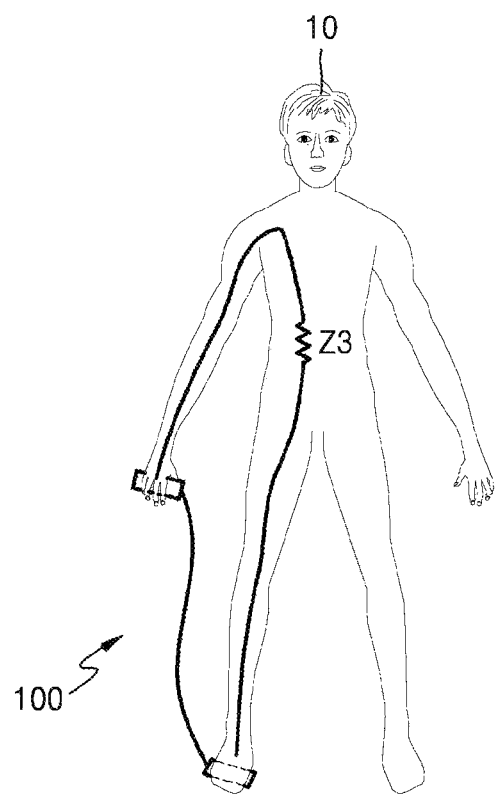
Figure 6D:
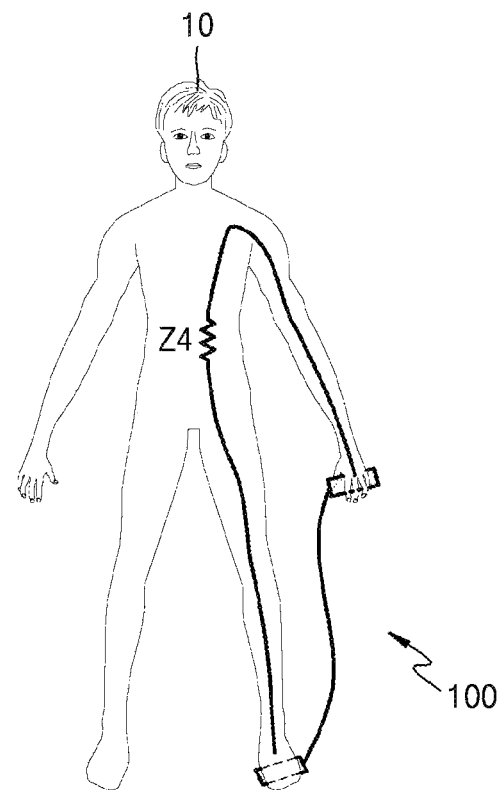
Figure 6E:
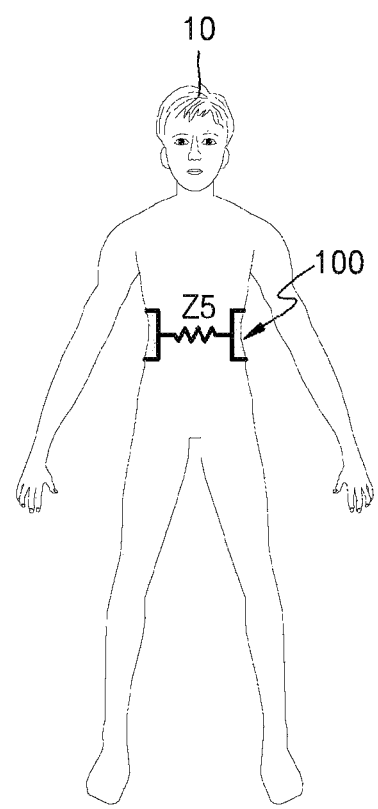

As illustrated in FIG. 6A, a user 10 may grab the first module 110 and the second module 120 with both hands, respectively. Since a current loop is formed through the first module 110, the body of the user 10, and the second module 120, the body impedance measuring apparatus 100 may measure an upper-body impedance Z1. Also, as illustrated in FIG. 6B, the user 10 may contact the first module 110 and the second module 120 with his or her feet. In this case, the body impedance measuring apparatus 100 may measure a lower-body impedance Z2. As illustrated in FIGS. 6C and 6D, the user 10 may contact the first module 110 with one hand and the second module 120 with one foot. In this case, the body impedance measuring apparatus 100 may measure a left-body impedance Z3 and a right-body impedance Z4. Through a combination of the configurations illustrated in FIGS. 6A to 6D, the whole-body impedance of the user 10 may be calculated. It is obvious that body impedances of other portions of the user 10 may be measured. As illustrated in FIG. 6E, the user 10 may contact the first module 110 and the second module 120 with both sides of the abdomen of the user 10. In this case, the body impedance measuring apparatus 100 may measure an abdomen impedance Z5.

In this way, the body impedance measuring apparatus 100 according to an exemplary embodiment may measure impedances of various portions of the body of the subject. In addition, even when a target of interest is a specific portion of the subject, it is possible to calculate body impedances at various positions, thus improving the exactness of the body impedance at the specific portion the subject.

Figure 7:
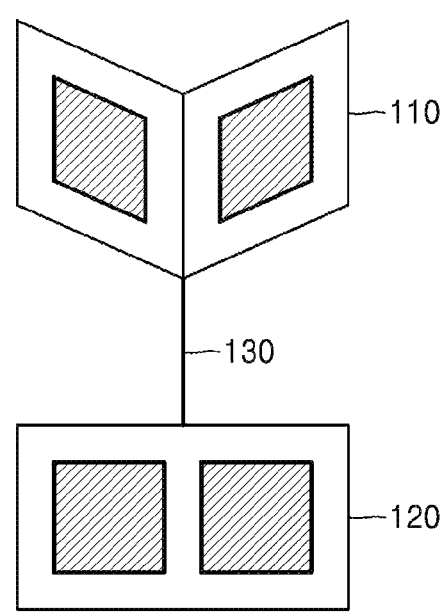
FIGS. 7 and 8 are diagrams of body impedance measuring apparatuses according to various exemplary embodiments.
Figure 8:
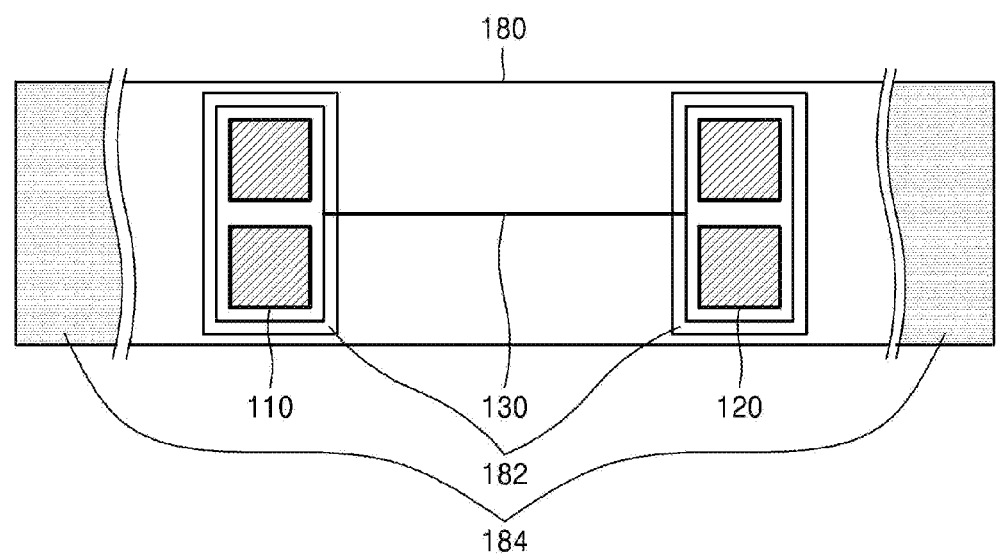

FIGS. 7 and 8 are diagrams of the body impedance measuring apparatus 100 according to various exemplary embodiments. At least one of the first and second modules 110 and 120 of the body impedance measuring apparatus 100 may be configured to be foldable at the central portion thereof. FIG. 7 illustrates a foldable structure of the first module 110. The first module 110 may be divided into a first region in which the first input electrode 111 is exposed and a second region in which the first output electrode 112 is exposed. The first region and the second region may be connected to each other by a hinge. Therefore, the first input electrode 111 may be rotatable around the first output electrode 112. The first module 110 may be foldable in a state in which the input electrode and the output electrode are exposed to the outside. The user may grab the first module 110 in a state in which the first input electrode 111 and the first output electrode 112 come into contact with each other. In this case, the first module 110 is folded, which allows the user to more firmly grab the first module 110.

As illustrated in FIG. 8, the body impedance measuring apparatus 100 may further include a patch 180 that fixes the first module 110 and the second module 120 while maintaining the distance between the first module 110 and the second module 120 constant. On one surface of the patch 180, a first fixing member 182 that fixes the first module 110 and the second module 120 and a second fixing member 184 that fixes the patch 180 to the subject may be provided. The first fixing member 182 may be made of a material having a sufficient adhesive strength to attach the first and second modules 110 and 120 thereto, and the second fixing member 184 may be made of a material capable of attaching to itself. For example, an adhesive layer may be disposed on a rear surface on which the input electrode and the output electrode of the first and second modules 110 and 120 are not disposed. Therefore, the rear surface may be attached to the first fixing member 182. After fixing the first and second modules 110 and 120 to the first fixing member 182 of the patch 180, the user may fix the second fixing member 184 to a region of interest of the subject, for example, the subject's abdomen, arm, or the like. The use of the patch 180 removes a need for the user to hold the body impedance measuring apparatus 100.

Figure 9:
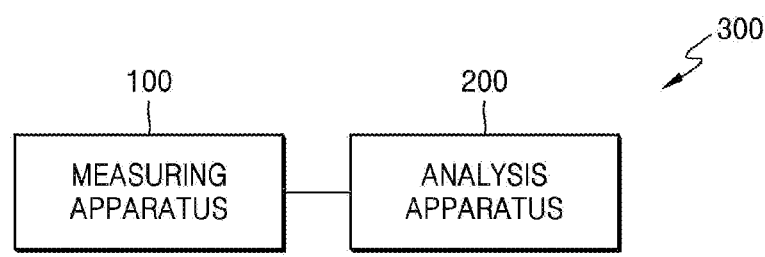
FIG. 9 is a block diagram of a body composition analysis system according to an exemplary embodiment.
Figure 10:
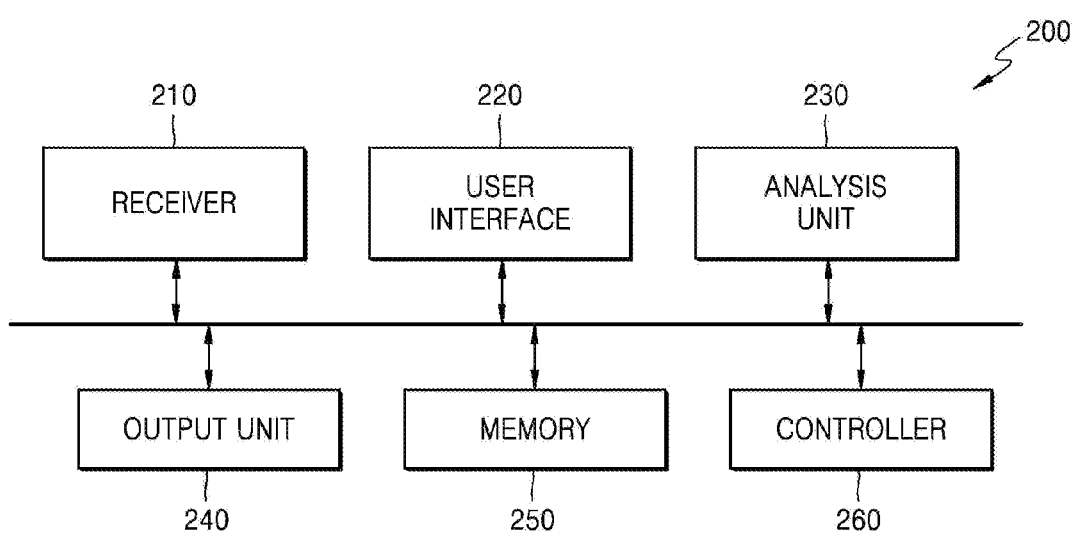
FIG. 10 is a block diagram of the body composition analysis system of FIG. 9.

The body composition of the subject may be analyzed by using the body impedance measured by the body impedance measuring apparatus 100 as described above. FIG. 9 is a block diagram of a body composition analysis system 300 according to an exemplary embodiment, and FIG. 10 is a block diagram of a body composition analysis apparatus 200 of FIG. 9. As illustrated in FIGS. 9 and 10, the body composition analysis system 300 may include a body impedance measuring apparatus (also referred to as a "measuring apparatus") 100 that measures a body impedance of a subject and a body composition analysis apparatus (also referred to as an "analysis apparatus") 200 that analyzes body composition based on the body impedance. Since the body impedance measuring apparatus 100 has been described above, a detailed description thereof is omitted.

The analysis apparatus 200 analyzes body composition based on the body impedance and provides to the user a protocol of the measuring apparatus 100 for measuring body impedance, for example, how to use the measuring apparatus 100, the order of directions in the measuring apparatus 100, or the like. The instruction order of the measuring apparatus 100 may vary depending on at which portion the user measures body impedance. In the case of measuring the body impedance of the entire body, the analysis apparatus 200 may provide an instruction order, such as a measurement of a body impedance between a left hand and a right hand, a measurement of a body impedance between a left foot and a left hand, a measurement of a body impedance between a left foot and a right foot, and a measurement of a body impedance between a right foot and a right hand. In addition, in the case of measuring the upper body, the analysis apparatus 200 may provide a guide that guides a subject to contact a left hand with a right hand. Alternatively, in the case of measuring a specific portion, the analysis apparatus 200 may provide a guide that guides a subject to bend the subject's arm or leg or to sit down or stand up.

The analysis apparatus 200 may include a receiver 210 that is able to communicate with the measuring apparatus 100, a user interface 220 that receives a user input or the like, an analysis unit 230 that analyzes body composition by using a body impedance received from the measuring apparatus 100, an output unit 240 that outputs information about the analyzed body composition, a memory 250 that stores a program or the like to be used by the body composition analysis system 300, and a controller 260 that controls components of the body composition analysis system 300. The analysis apparatus 200 may be an independent apparatus or may be implemented by using an application of another apparatus. For example, the analysis apparatus 200 may be a mobile terminal.

The user interface 220 may receive an input for operating the analysis apparatus 200 from the user or may output at least one piece of information about body composition processed by the analysis apparatus 200. The user interface 220 may include a button, a keypad, a switch, a dial, or a touch interface to be used by the user so as to directly operate the analysis apparatus 200. The user may input supplementary data, such as the age, weight, height, or gender of the subject, through the user interface 220.

The analysis unit 230 may analyze the body composition by using the body impedance. In this case, the body composition may include a body fat mass, a skin characteristic (for example, body water), a muscle strength, a presence or absence of edema, a skeletal muscle mass, a muscle mass, a fat index, a body composition ratio, a visceral fat mass, or the like.

In addition, the analysis unit 230 may analyze body composition with reference to supplementary information of the subject, in addition to the body impedances.

The output unit 240 may output information about the subject as well as the body composition. The output unit 240 may be a display that displays the information through images or text, or a sound output unit (speaker) that outputs the information at an audible frequency. The output unit 240 may include both of the display and the sound output unit. The controller 260 may control the entire operation of the body composition analysis system 300. For example, the controller 260 may control the measuring apparatus 100 so as to measure the body impedance. Specifically, the controller 260 may provide a protocol of the measuring apparatus 100 for measuring body impedance to the user through the output unit 240.

In the body composition analysis system 300, the measuring apparatus 100 and the analysis apparatus 200 have been described as being separately provided. However, this is only for convenience of description and an exemplary embodiment is not limited thereto. It is obvious that the body composition analysis system 300 may be implemented as a single apparatus. For example, components of the analysis apparatus 200 may be included in the measuring apparatus 100.

It is possible to measure impedances of various portions of a subject by using a single body impedance measuring apparatus. The body impedance measuring apparatus according to an exemplary embodiment may be portable.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A body impedance measuring apparatus comprising:
    a first module comprising a first input electrode and a first output electrode which are configured to contact a subject;
    a second module comprising a second input electrode and a second output electrode which are configured to contact the subject;
    a connection member configured to connect the first module to the second module that is paired with the first module and adjust a length of an exposed portion of the connection member according to a distance between the first module and the second module; and
    a measuring unit configured to apply a current to the first and second input electrodes, detect a voltage between the first and second output electrodes, and determine a body impedance of the subject based on the detected voltage,
    wherein the connection member comprises:
        a cable configured to connect the first module to the second module;
        a rotatable member around which the cable is wound; and
        a restoring member configured to exert a restoring force, based on a rotation of the rotatable member, in response to the distance between the first module and the second module being increased by an external force, and
    the distance between the first module and the second module is reduced by the restoring force in response to the external force being removed,
    the first module is disposed on a fixing member divided into a first area and a second area,
    the first input electrode and the first output electrode are respectively disposed in the first area and the second area of a front surface of the fixing member, and
    the first module is half-folded in a state in which the first input electrode and the first output electrode are exposed outside the first module to be configured to respectively contact with a first point and a second point in a hand of the subject, and the first area of a rear surface of the fixing member is entirely in contact with the second area of the rear surface, while the measuring unit applies the current to the first input electrode in contact with the first point in the hand and detects the voltage from the first output electrode in contact with the second point in the hand.

2. The body impedance measuring apparatus of claim 1, wherein the connection member comprises a first wire configured to connect the measuring unit to the second input electrode, and a second wire configured to connect the measuring unit to the second output electrode.

3. The body impedance measuring apparatus of claim 1, wherein the first module comes into contact with the second module in response to the external force being removed.

4. The body impedance measuring apparatus of claim 1, wherein the measuring unit comprises:
    a current supply configured to supply the current to the first and second input electrodes;
    a voltage detector configured to detect the voltage between the first and second output electrodes; and
    an impedance calculator configured to calculate the body impedance of the subject from the voltage,
    wherein at least one of the current supply, the voltage detector, and the impedance calculator is disposed in the first module.

5. The body impedance measuring apparatus of claim 1, wherein one of the first module and the second module is configured to contact a foot of the subject.

6. The body impedance measuring apparatus of claim 1, further comprising a patch configured to fix the first and second modules while maintaining the distance between the first module and the second module to be constant,
    wherein the patch is detachable from the subject.

7. The body impedance measuring apparatus of claim 1, further comprising a transmitter configured to transmit information of the body impedance to an external device.

8. A body composition analysis system comprising:
    a measuring apparatus comprising:
        a first module and a second module, each of the first module and the second module comprising an input electrode and an output electrode which are configured to contact a subject;
        a connection member configured to connect the first module to the second module that is paired with the first module, and adjust a length of an exposed portion of the connection member according to a distance between the first module and the second module; and
        a measuring unit configured to supply a current to the input electrodes, detect a voltage between the output electrodes, and determine a body impedance of the subject,
    an analysis apparatus configured to provide a protocol of using the measuring apparatus for determining the body impedance, wherein
    the input electrode and the output electrode of the first module correspond to a first input electrode and a first output electrode, respectively,
    the first module is disposed on a fixing member divided into a first area and a second area,
    the first input electrode and the first output electrode of the first module are respectively disposed in the first area and the second area of a front surface of the fixing member, and
    the first module is half-folded in a state in which the first input electrode and the first output electrode are exposed outside the first module to be configured to respectively contact with a first point and a second point in a hand of the subject, and the first area of a rear surface of the fixing member is entirely in contact with the second area of the rear surface, while the measuring unit applies the current to the first input electrode in contact with the first point in the hand and detects the voltage from the first output electrode in contact with the second point in the hand.

9. The body composition analysis system of claim 8, wherein the analysis apparatus is further configured to receive information of the body impedance from the measuring apparatus through wireless communication and analyze body composition of the subject based on the information of the body impedance.

10. The body composition analysis system of claim 9, wherein the body composition comprises at least one of a body fat mass, a skeletal muscle mass, a muscle mass, a fat index, a muscle strength, edema, a body composition ratio, and a visceral fat mass.

11. The body composition analysis system of claim 9, wherein the analysis apparatus comprises a display configured to display the body composition.

12. The body composition analysis system of claim 9, wherein the analysis apparatus comprises a user interface configured to receive an input of at least one of a weight, an age, a gender and a height of the subject.

13. The body composition analysis system of claim 8, wherein at least a component of the measuring unit is disposed in the first module and is electrically connected to the second module through the connection member.

* * * * *